US008845677B2

(12) United States Patent
Pal

(10) Patent No.: US 8,845,677 B2
(45) Date of Patent: *Sep. 30, 2014

(54) RETRIEVABLE DEVICE HAVING A RETICULATION PORTION WITH STAGGERED STRUTS

(75) Inventor: Dharmendra Pal, Wilmington, MA (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/336,031

(22) Filed: Dec. 23, 2011

(65) Prior Publication Data

US 2012/0095543 A1  Apr. 19, 2012

Related U.S. Application Data

(63) Continuation of application No. 11/455,421, filed on Jun. 19, 2006, now Pat. No. 8,109,962.

(60) Provisional application No. 60/692,317, filed on Jun. 20, 2005.

(51) Int. Cl.
| | |
|---|---|
| *A61M 29/00* | (2006.01) |
| *A61F 2/01* | (2006.01) |
| *A61F 2/91* | (2013.01) |
| *A61F 2/915* | (2013.01) |
| *A61F 2/95* | (2013.01) |

(52) U.S. Cl.
CPC ....... *A61F 2/013* (2013.01); *A61F 2002/91508* (2013.01); *A61F 2002/91558* (2013.01); *A61F 2002/91533* (2013.01); *A61F 2230/008* (2013.01); *A61F 2002/9528* (2013.01); *A61F 2/915* (2013.01); *A61F 2/91* (2013.01); *A61F 2230/0006* (2013.01); *A61F 2002/018* (2013.01); *A61F 2002/91525* (2013.01)
USPC ............ 606/200; 606/113; 606/114; 606/127

(58) Field of Classification Search
CPC ............ A61F 2/013; A61F 2/91; A61F 2/915
USPC .......... 606/200, 113, 114, 127; 623/1.1, 1.15, 623/1.22, 1.11, 1.49
See application file for complete search history.

(56) References Cited

U.S. PATENT DOCUMENTS

| | | |
|---|---|---|
| 3,547,103 A | 12/1970 | Cook |
| 3,635,223 A | 1/1972 | Klieman |

(Continued)

FOREIGN PATENT DOCUMENTS

| | | |
|---|---|---|
| WO | WO 96/10591 | 4/1996 |
| WO | WO 99/44510 | 9/1999 |

*Primary Examiner* — Tuan V Nguyen
*Assistant Examiner* — Tin Nguyen
(74) *Attorney, Agent, or Firm* — Brinks Gilson & Lione

(57) ABSTRACT

A retrievable device for treatment of a stenotic lesion in a body vessel is disclosed. The device comprises a reticulation portion including a plurality of struts connected together in a singly staggered configuration distally along a longitudinal axis. The plurality of struts of the reticulation portion is configured to fold along the longitudinal axis defining a collapsed state of the device for retrieval. The device further includes an expandable body distally extending from the reticulation portion along an outer diameter for treatment of the stenotic lesion. The expandable body is configured to expand in the open state and collapsed in the collapsed state of the reticulation portion for retrieval. The device further comprises a retrieval stem extending proximally from the reticulation portion for retrieval of the device in the collapsed state.

8 Claims, 5 Drawing Sheets

(56) References Cited

U.S. PATENT DOCUMENTS

| | | |
|---|---|---|
| 3,923,065 A | 12/1975 | Nozick et al. |
| 3,952,747 A | 4/1976 | Kimmell, Jr. |
| 3,978,863 A | 9/1976 | Fettel et al. |
| 3,996,938 A | 12/1976 | Clark, III |
| 4,425,908 A | 1/1984 | Simon |
| 4,494,531 A | 1/1985 | Gianturco |
| 4,548,206 A | 10/1985 | Osborne |
| 4,561,439 A | 12/1985 | Bishop et al. |
| 4,619,246 A | 10/1986 | Molgaard-Nielsen et al. |
| 4,643,184 A | 2/1987 | Mobin-Uddin |
| 4,646,736 A | 3/1987 | Auth |
| 4,650,472 A | 3/1987 | Bates |
| 4,665,906 A | 5/1987 | Jervis |
| 4,669,464 A | 6/1987 | Sulepov |
| 4,688,553 A | 8/1987 | Metals |
| 4,723,549 A | 2/1988 | Wholey et al. |
| 4,727,873 A | 3/1988 | Mobin-Uddin |
| 4,817,600 A | 4/1989 | Herms et al. |
| 4,824,435 A | 4/1989 | Giesy et al. |
| 4,832,055 A | 5/1989 | Palestrant |
| 4,873,978 A | 10/1989 | Ginsburg |
| 4,943,297 A | 7/1990 | Saveliev et al. |
| 4,957,501 A | 9/1990 | Lahille et al. |
| 4,990,156 A | 2/1991 | Lefebvre |
| 5,053,008 A | 10/1991 | Bajaj |
| 5,059,205 A | 10/1991 | El-Nounou et al. |
| 5,069,226 A | 12/1991 | Yamauchi et al. |
| 5,100,423 A | 3/1992 | Fearnot |
| 5,108,418 A | 4/1992 | Lefebvre |
| 5,108,419 A | 4/1992 | Reger et al. |
| 5,112,347 A | 5/1992 | Taheri |
| 5,129,890 A | 7/1992 | Bates et al. |
| 5,133,733 A | 7/1992 | Rasmussen et al. |
| 5,147,379 A | 9/1992 | Sabbaghian et al. |
| 5,152,777 A | 10/1992 | Goldberg |
| 5,160,342 A | 11/1992 | Reger |
| 5,234,458 A | 8/1993 | Metais |
| 5,242,462 A | 9/1993 | El-Nounou |
| 5,243,996 A | 9/1993 | Hall |
| 5,251,640 A | 10/1993 | Osborne |
| 5,263,964 A | 11/1993 | Purdy |
| 5,300,086 A | 4/1994 | Gory et al. |
| 5,324,304 A | 6/1994 | Rasmussen |
| 5,329,942 A | 7/1994 | Gunther et al. |
| 5,344,427 A | 9/1994 | Cottenceau et al. |
| 5,350,398 A | 9/1994 | Pavcnik et al. |
| 5,370,657 A | 12/1994 | Irie |
| 5,375,612 A | 12/1994 | Cottenceau et al. |
| 5,383,887 A | 1/1995 | Nadal |
| 5,413,586 A | 5/1995 | Dibie et al. |
| 5,415,630 A | 5/1995 | Gory et al. |
| 5,417,708 A | 5/1995 | Hall et al. |
| 5,527,338 A | 6/1996 | Purdy |
| 5,531,788 A | 7/1996 | Dibie et al. |
| 5,549,626 A | 8/1996 | Miller et al. |
| 5,562,698 A | 10/1996 | Parker |
| 5,601,595 A | 2/1997 | Smith |
| 5,624,461 A | 4/1997 | Mariant |
| 5,626,605 A | 5/1997 | Irie et al. |
| 5,634,942 A | 6/1997 | Chevillon et al. |
| 5,649,953 A | 7/1997 | Lefebvre |
| 5,669,933 A | 9/1997 | Simon et al. |
| 5,681,347 A | 10/1997 | Cathcart et al. |
| 5,690,667 A | 11/1997 | Gia |
| 5,693,067 A | 12/1997 | Purdy |
| 5,695,518 A | 12/1997 | Laerum |
| 5,695,519 A | 12/1997 | Summers et al. |
| 5,709,704 A | 1/1998 | Nott et al. |
| 5,713,853 A | 2/1998 | Clark et al. |
| 5,720,764 A | 2/1998 | Naderlinger |
| 5,725,550 A | 3/1998 | Nadal |
| 5,746,767 A | 5/1998 | Smith |
| 5,755,790 A | 5/1998 | Chevillon et al. |
| 5,769,816 A | 6/1998 | Barbut et al. |
| 5,769,871 A | 6/1998 | Mers et al. |
| 5,795,322 A | 8/1998 | Boudewijn |
| 5,800,457 A | 9/1998 | Gelbfish et al. |
| 5,800,525 A | 9/1998 | Bachinski et al. |
| 5,810,874 A | 9/1998 | Lefebvre |
| 5,814,064 A | 9/1998 | Daniel et al. |
| 5,827,324 A | 10/1998 | Cassell et al. |
| 5,830,230 A | 11/1998 | Berryman et al. |
| 5,836,968 A | 11/1998 | Simon et al. |
| 5,836,969 A | 11/1998 | Kim et al. |
| 5,846,260 A | 12/1998 | Maahs |
| 5,853,420 A | 12/1998 | Chevillon et al. |
| 5,876,367 A | 3/1999 | Kaganov et al. |
| 5,893,869 A | 4/1999 | Barnhart et al. |
| 5,895,391 A | 4/1999 | Farnholtz |
| 5,895,399 A | 4/1999 | Barbut et al. |
| 5,895,410 A | 4/1999 | Forber et al. |
| 5,908,435 A | 6/1999 | Samuels |
| 5,910,154 A | 6/1999 | Tsugita et al. |
| 5,911,704 A | 6/1999 | Humes |
| 5,911,717 A | 6/1999 | Jacobsen et al. |
| 5,911,734 A | 6/1999 | Tsugita et al. |
| 5,919,224 A | 7/1999 | Thompson et al. |
| 5,925,062 A | 7/1999 | Purdy |
| 5,925,063 A | 7/1999 | Khosravi |
| 5,928,260 A | 7/1999 | Chine et al. |
| 5,928,261 A | 7/1999 | Ruiz |
| 5,938,683 A | 8/1999 | Lefebvre |
| 5,941,896 A | 8/1999 | Kerr |
| 5,944,728 A | 8/1999 | Bates |
| 5,947,985 A | 9/1999 | Imran |
| 5,947,995 A | 9/1999 | Samuels |
| 5,948,017 A | 9/1999 | Taheri |
| 5,951,567 A | 9/1999 | Javier, Jr. et al. |
| 5,954,741 A | 9/1999 | Fox |
| 5,954,742 A | 9/1999 | Osypka |
| 5,954,745 A | 9/1999 | Gertler et al. |
| 5,968,057 A | 10/1999 | Taheri |
| 5,968,071 A | 10/1999 | Chevillon et al. |
| 5,972,019 A | 10/1999 | Engelson et al. |
| 5,976,162 A | 11/1999 | Doan et al. |
| 5,976,172 A | 11/1999 | Homsma et al. |
| 5,980,555 A | 11/1999 | Barbut et al. |
| 5,984,947 A | 11/1999 | Smith |
| 5,989,281 A | 11/1999 | Barbut et al. |
| 6,001,118 A | 12/1999 | Daniel et al. |
| 6,007,557 A | 12/1999 | Ambrisco et al. |
| 6,007,558 A | 12/1999 | Ravenscroft et al. |
| 6,010,522 A | 1/2000 | Barbut et al. |
| 6,013,093 A | 1/2000 | Nott et al. |
| 6,015,424 A | 1/2000 | Rosenbluth et al. |
| 6,027,520 A | 2/2000 | Tsugita et al. |
| 6,036,717 A | 3/2000 | Mers Kelly et al. |
| 6,036,720 A | 3/2000 | Abrams et al. |
| 6,042,598 A | 3/2000 | Tsugita et al. |
| 6,051,014 A | 4/2000 | Jang |
| 6,051,015 A | 4/2000 | Maahs |
| 6,053,932 A | 4/2000 | Daniel et al. |
| 6,059,745 A | 5/2000 | Gelbfish |
| 6,059,814 A | 5/2000 | Ladd |
| 6,063,113 A | 5/2000 | Kavteladze et al. |
| 6,066,158 A | 5/2000 | Engelson et al. |
| 6,068,645 A | 5/2000 | Tu |
| 6,074,357 A | 6/2000 | Kaganov et al. |
| 6,077,274 A | 6/2000 | Ouchi et al. |
| 6,080,178 A | 6/2000 | Meglin |
| 6,083,239 A | 7/2000 | Addis |
| 6,086,577 A | 7/2000 | Ken et al. |
| 6,086,605 A | 7/2000 | Barbut et al. |
| 6,093,199 A | 7/2000 | Brown et al. |
| 6,096,053 A | 8/2000 | Bates |
| 6,099,549 A | 8/2000 | Bosma et al. |
| 6,106,497 A | 8/2000 | Wang |
| 6,126,672 A | 10/2000 | Berryman et al. |
| 6,126,673 A | 10/2000 | Kim et al. |
| 6,129,739 A | 10/2000 | Khosravi |
| 6,136,016 A | 10/2000 | Barbut et al. |
| 6,146,396 A | 11/2000 | Konya et al. |
| 6,146,404 A | 11/2000 | Kim et al. |
| 6,152,931 A | 11/2000 | Nadal et al. |

(56) References Cited

U.S. PATENT DOCUMENTS

| | | |
|---|---|---|
| 6,152,946 A | 11/2000 | Broome et al. |
| 6,152,947 A | 11/2000 | Ambrisco et al. |
| 6,156,061 A | 12/2000 | Wallace et al. |
| 6,159,230 A | 12/2000 | Samuels |
| 6,165,179 A | 12/2000 | Cathcart et al. |
| 6,165,198 A | 12/2000 | McGurk et al. |
| 6,165,199 A | 12/2000 | Barbut |
| 6,165,200 A | 12/2000 | Tsugita et al. |
| 6,168,579 B1 | 1/2001 | Tsugita |
| 6,168,603 B1 | 1/2001 | Leslie et al. |
| 6,168,622 B1 | 1/2001 | Mazzocchi |
| 6,171,327 B1 | 1/2001 | Daniel et al. |
| 6,171,328 B1 | 1/2001 | Addis |
| 6,174,318 B1 | 1/2001 | Bates et al. |
| 6,179,851 B1 | 1/2001 | Barbut et al. |
| 6,179,859 B1 | 1/2001 | Bates et al. |
| 6,179,860 B1 | 1/2001 | Fulton, III et al. |
| 6,179,861 B1 | 1/2001 | Khosravi et al. |
| 6,187,025 B1 | 2/2001 | Machek |
| 6,193,739 B1 | 2/2001 | Chevillon et al. |
| 6,203,561 B1 | 3/2001 | Ramee et al. |
| 6,214,025 B1 | 4/2001 | Thistle et al. |
| 6,214,026 B1 | 4/2001 | Lepak et al. |
| 6,221,091 B1 | 4/2001 | Khosravi |
| 6,224,620 B1 | 5/2001 | Maahs |
| 6,231,588 B1 | 5/2001 | Zadno-Azizi |
| 6,231,589 B1 | 5/2001 | Wessman et al. |
| 6,235,044 B1 | 5/2001 | Root et al. |
| 6,235,045 B1 | 5/2001 | Barbut et al. |
| 6,238,412 B1 | 5/2001 | Dubrul et al. |
| 6,241,746 B1 | 6/2001 | Bosma et al. |
| 6,245,087 B1 | 6/2001 | Addis |
| 6,245,088 B1 | 6/2001 | Lowery |
| 6,245,089 B1 | 6/2001 | Daniel et al. |
| 6,251,122 B1 | 6/2001 | Tsukernik |
| 6,254,550 B1 | 7/2001 | McNamara et al. |
| 6,254,633 B1 | 7/2001 | Pinchuk et al. |
| 6,258,026 B1 | 7/2001 | Ravenscroft et al. |
| 6,258,115 B1 | 7/2001 | Dubrul |
| 6,258,120 B1 | 7/2001 | McKenzie et al. |
| 6,261,305 B1 | 7/2001 | Marotta et al. |
| 6,264,672 B1 | 7/2001 | Fisher |
| 6,267,776 B1 | 7/2001 | O'Connell |
| 6,267,777 B1 | 7/2001 | Bosma et al. |
| 6,273,900 B1 | 8/2001 | Nott et al. |
| 6,273,901 B1 | 8/2001 | Whitcher et al. |
| 6,277,125 B1 | 8/2001 | Barry et al. |
| 6,277,126 B1 | 8/2001 | Barry et al. |
| 6,277,138 B1 | 8/2001 | Levinson et al. |
| 6,277,139 B1 | 8/2001 | Levinson et al. |
| 6,280,451 B1 | 8/2001 | Bates et al. |
| 6,287,321 B1 | 9/2001 | Jang |
| 6,290,710 B1 | 9/2001 | Cryer et al. |
| 6,306,163 B1 | 10/2001 | Fitz |
| 6,309,399 B1 | 10/2001 | Barbut et al. |
| 6,312,444 B1 | 11/2001 | Barbut |
| 6,319,268 B1 | 11/2001 | Ambrisco et al. |
| 6,325,815 B1 | 12/2001 | Kusleika et al. |
| 6,325,816 B1 | 12/2001 | Fulton, III et al. |
| 6,328,755 B1 | 12/2001 | Marshall |
| 6,331,183 B1 | 12/2001 | Suon |
| 6,331,184 B1 | 12/2001 | Abrams |
| 6,334,864 B1 | 1/2002 | Amplatz et al. |
| 6,336,934 B1 | 1/2002 | Gilson et al. |
| 6,340,364 B2 | 1/2002 | Kanesaka |
| 6,342,062 B1 | 1/2002 | Suon et al. |
| 6,342,063 B1 | 1/2002 | DeVries et al. |
| 6,344,048 B1 | 2/2002 | Chin et al. |
| 6,344,049 B1 | 2/2002 | Levinson et al. |
| 6,346,116 B1 | 2/2002 | Brooks et al. |
| 6,348,041 B1 | 2/2002 | Klint |
| 6,348,063 B1 | 2/2002 | Yassour et al. |
| 6,355,051 B1 | 3/2002 | Sisskind et al. |
| 6,358,228 B1 | 3/2002 | Tubman et al. |
| 6,361,545 B1 | 3/2002 | Macoviak et al. |
| 6,361,546 B1 | 3/2002 | Khosravi |
| 6,361,547 B1 | 3/2002 | Hieshima |
| 6,364,895 B1 | 4/2002 | Greenhalgh |
| 6,364,896 B1 | 4/2002 | Addis |
| 6,368,338 B1 | 4/2002 | Konya et al. |
| 6,371,969 B1 | 4/2002 | Tsugita et al. |
| 6,371,970 B1 | 4/2002 | Khosravi et al. |
| 6,371,971 B1 | 4/2002 | Tsugita et al. |
| 6,375,670 B1 | 4/2002 | Greenhalgh |
| 6,379,374 B1 | 4/2002 | Hieshima et al. |
| 6,383,146 B1 | 5/2002 | Klint |
| 6,383,174 B1 | 5/2002 | Eder |
| 6,383,193 B1 | 5/2002 | Cathcart et al. |
| 6,383,196 B1 | 5/2002 | Leslie et al. |
| 6,383,205 B1 | 5/2002 | Samson et al. |
| 6,383,206 B1 | 5/2002 | Gillick et al. |
| 6,391,044 B1 | 5/2002 | Yadav et al. |
| 6,391,045 B1 | 5/2002 | Kim et al. |
| 6,395,014 B1 | 5/2002 | Macoviak et al. |
| 6,402,771 B1 | 6/2002 | Palmer et al. |
| 6,402,772 B1 | 6/2002 | Amplatz et al. |
| 6,409,742 B1 | 6/2002 | Fulton, III et al. |
| 6,413,235 B1 | 7/2002 | Parodi |
| 6,416,530 B2 | 7/2002 | DeVries et al. |
| 6,419,686 B1 | 7/2002 | McLeod et al. |
| 6,423,086 B1 | 7/2002 | Barbut et al. |
| 6,425,909 B1 | 7/2002 | Dieck et al. |
| 6,428,557 B1 | 8/2002 | Hilaire |
| 6,428,558 B1 | 8/2002 | Jones et al. |
| 6,428,559 B1 | 8/2002 | Johnson |
| 6,432,122 B1 | 8/2002 | Gilson et al. |
| 6,436,112 B2 | 8/2002 | Wensel et al. |
| 6,436,120 B1 | 8/2002 | Meglin |
| 6,436,121 B1 | 8/2002 | Blom |
| 6,443,926 B1 | 9/2002 | Kletschka |
| 6,443,971 B1 | 9/2002 | Boylan et al. |
| 6,443,972 B1 | 9/2002 | Bosma et al. |
| 6,447,530 B1 | 9/2002 | Ostrovsky et al. |
| 6,447,531 B1 | 9/2002 | Amplatz |
| 6,458,139 B1 | 10/2002 | Palmer et al. |
| 6,458,145 B1 | 10/2002 | Ravenscroft et al. |
| 6,461,370 B1 | 10/2002 | Gray et al. |
| 6,468,290 B1 | 10/2002 | Weldon et al. |
| 6,468,291 B2 | 10/2002 | Bates et al. |
| 6,482,222 B1 | 11/2002 | Bruckheimer et al. |
| 6,485,456 B1 | 11/2002 | Kletschka |
| 6,485,500 B1 | 11/2002 | Kokish et al. |
| 6,485,501 B1 | 11/2002 | Green |
| 6,485,502 B2 | 11/2002 | Michael et al. |
| 6,491,712 B1 | 12/2002 | O'Connor |
| 6,494,895 B2 | 12/2002 | Addis |
| 6,497,709 B1 | 12/2002 | Heath |
| 6,499,487 B1 | 12/2002 | McKenzie et al. |
| 6,500,166 B1 | 12/2002 | Zadno Azizi et al. |
| 6,500,191 B2 | 12/2002 | Addis |
| 6,502,606 B2 | 1/2003 | Klint |
| 6,506,203 B1 | 1/2003 | Boyle et al. |
| 6,506,205 B2 | 1/2003 | Goldberg et al. |
| 6,508,826 B2 | 1/2003 | Murphy et al. |
| 6,511,492 B1 | 1/2003 | Rosenbluth et al. |
| 6,511,496 B1 | 1/2003 | Huter et al. |
| 6,511,497 B1 | 1/2003 | Braun et al. |
| 6,511,503 B1 | 1/2003 | Burkett et al. |
| 6,514,273 B1 | 2/2003 | Voss et al. |
| 6,517,559 B1 | 2/2003 | O'Connell |
| 6,520,978 B1 | 2/2003 | Blackledge et al. |
| 6,527,746 B1 | 3/2003 | Oslund et al. |
| 6,527,791 B2 | 3/2003 | Fisher |
| 6,527,962 B1 | 3/2003 | Nadal |
| 6,530,935 B2 | 3/2003 | Wensel et al. |
| 6,530,939 B1 | 3/2003 | Hopkins et al. |
| 6,530,940 B2 | 3/2003 | Fisher |
| 6,533,800 B1 | 3/2003 | Barbut |
| 6,537,293 B1 | 3/2003 | Berryman et al. |
| 6,537,294 B1 | 3/2003 | Boyle et al. |
| 6,537,296 B2 | 3/2003 | Levinson et al. |
| 6,537,297 B2 | 3/2003 | Tsugita et al. |
| 6,540,722 B1 | 4/2003 | Boyle et al. |
| 6,540,767 B1 | 4/2003 | Walak et al. |

(56) References Cited

U.S. PATENT DOCUMENTS

| | | |
|---|---|---|
| 6,540,768 B1 | 4/2003 | Diaz et al. |
| 6,544,221 B1 | 4/2003 | Kokish et al. |
| 6,544,276 B1 | 4/2003 | Azizi |
| 6,544,279 B1 | 4/2003 | Hopkins et al. |
| 6,544,280 B1 | 4/2003 | Daniel et al. |
| 6,547,759 B1 | 4/2003 | Fisher |
| 6,551,303 B1 | 4/2003 | Van Tassel et al. |
| 6,551,341 B2 | 4/2003 | Boylan et al. |
| 6,551,342 B1 * | 4/2003 | Shen et al. .............. 606/200 |
| 6,554,849 B1 | 4/2003 | Jones et al. |
| 6,558,404 B2 | 5/2003 | Tsukernik |
| 6,558,405 B1 | 5/2003 | McInnes |
| 6,558,406 B2 | 5/2003 | Okada |
| 6,562,058 B2 | 5/2003 | Seguin et al. |
| 6,565,591 B2 | 5/2003 | Brady et al. |
| 6,569,147 B1 | 5/2003 | Evans et al. |
| 6,569,183 B1 | 5/2003 | Kim et al. |
| 6,569,184 B2 | 5/2003 | Huter |
| 6,575,995 B1 | 6/2003 | Huter et al. |
| 6,575,996 B1 | 6/2003 | Denison et al. |
| 6,575,997 B1 | 6/2003 | Palmer et al. |
| 6,579,303 B2 | 6/2003 | Amplatz |
| 6,582,396 B1 | 6/2003 | Parodi |
| 6,582,447 B1 | 6/2003 | Patel et al. |
| 6,582,448 B1 | 6/2003 | Boyle et al. |
| 6,589,230 B2 | 7/2003 | Gia et al. |
| 6,589,263 B1 | 7/2003 | Hopkins et al. |
| 6,589,264 B1 | 7/2003 | Barbut et al. |
| 6,589,265 B1 | 7/2003 | Palmer et al. |
| 6,589,266 B2 | 7/2003 | Whitcher et al. |
| 6,592,546 B1 | 7/2003 | Barbut et al. |
| 6,592,606 B2 | 7/2003 | Huter et al. |
| 6,596,011 B2 | 7/2003 | Johnson et al. |
| 6,599,307 B1 | 7/2003 | Huter et al. |
| 6,599,308 B2 | 7/2003 | Amplatz |
| 6,602,271 B2 | 8/2003 | Adams et al. |
| 6,602,273 B2 | 8/2003 | Marshall |
| 6,605,102 B1 | 8/2003 | Mazzocchi et al. |
| 6,607,506 B2 | 8/2003 | Kletschka |
| 6,610,077 B1 | 8/2003 | Hancock et al. |
| 6,613,074 B1 | 9/2003 | Mitelberg et al. |
| 6,616,679 B1 | 9/2003 | Khosravi et al. |
| 6,616,680 B1 | 9/2003 | Thielen |
| 6,616,681 B2 | 9/2003 | Hanson et al. |
| 6,616,682 B2 | 9/2003 | Joergensen et al. |
| 6,620,148 B1 | 9/2003 | Tsugita |
| 6,620,182 B1 | 9/2003 | Khosravi et al. |
| 6,623,450 B1 | 9/2003 | Dutta |
| 6,623,506 B2 | 9/2003 | McGuckin, Jr. et al. |
| 6,629,953 B1 | 10/2003 | Boyd |
| 6,635,068 B1 | 10/2003 | Dubrul et al. |
| 6,635,069 B1 | 10/2003 | Teoh et al. |
| 6,635,070 B2 | 10/2003 | Leeflang et al. |
| 6,638,293 B1 | 10/2003 | Makower et al. |
| 6,638,294 B1 | 10/2003 | Palmer |
| 6,638,372 B1 | 10/2003 | Abrams et al. |
| 6,641,590 B1 | 11/2003 | Palmer et al. |
| 6,641,605 B1 | 11/2003 | Stergiopulos |
| 6,645,220 B1 | 11/2003 | Huter et al. |
| 6,645,221 B1 | 11/2003 | Richter |
| 6,645,222 B1 | 11/2003 | Parodi et al. |
| 6,645,223 B2 | 11/2003 | Boyle et al. |
| 6,645,224 B2 | 11/2003 | Gilson et al. |
| 6,652,554 B1 | 11/2003 | Wholey et al. |
| 6,652,557 B1 | 11/2003 | MacDonald |
| 6,652,558 B2 | 11/2003 | Patel et al. |
| 6,656,201 B2 | 12/2003 | Ferrera et al. |
| 6,656,202 B2 | 12/2003 | Papp et al. |
| 6,656,203 B2 | 12/2003 | Roth et al. |
| 6,656,204 B2 | 12/2003 | Ambrisco et al. |
| 6,656,351 B2 | 12/2003 | Boyle |
| 6,660,021 B1 | 12/2003 | Palmer et al. |
| 6,663,613 B1 | 12/2003 | Evans et al. |
| 6,663,650 B2 | 12/2003 | Sepetka et al. |
| 6,663,651 B2 | 12/2003 | Krolik et al. |
| 6,663,652 B2 | 12/2003 | Daniel et al. |
| 6,695,865 B2 | 2/2004 | Boyle et al. |
| 6,702,834 B1 | 3/2004 | Boylan et al. |
| 6,712,835 B2 | 3/2004 | Mazzocchi et al. |
| 6,726,701 B2 | 4/2004 | Gilson et al. |
| 6,758,855 B2 | 7/2004 | Fulton, III et al. |
| 6,761,727 B1 | 7/2004 | Ladd |
| 6,780,175 B1 | 8/2004 | Sachdeva et al. |
| 6,793,668 B1 | 9/2004 | Fisher |
| 6,866,677 B2 | 3/2005 | Douk et al. |
| 2001/0000799 A1 | 5/2001 | Wessman et al. |
| 2001/0001817 A1 | 5/2001 | Humes |
| 2001/0005789 A1 | 6/2001 | Root et al. |
| 2001/0007947 A1 | 7/2001 | Kanesaka |
| 2001/0011181 A1 | 8/2001 | DiMatteo |
| 2001/0011182 A1 | 8/2001 | Dubrul et al. |
| 2001/0012951 A1 | 8/2001 | Bates et al. |
| 2001/0016755 A1 | 8/2001 | Addis |
| 2001/0020175 A1 | 9/2001 | Yassour et al. |
| 2001/0023358 A1 | 9/2001 | Tsukernik |
| 2001/0025187 A1 | 9/2001 | Okada |
| 2001/0031980 A1 | 10/2001 | Wensel et al. |
| 2001/0031981 A1 | 10/2001 | Evans et al. |
| 2001/0031982 A1 | 10/2001 | Peterson et al. |
| 2001/0039431 A1 | 11/2001 | DeVries et al. |
| 2001/0039432 A1 | 11/2001 | Whitcher et al. |
| 2001/0041908 A1 | 11/2001 | Levinson et al. |
| 2001/0041909 A1 | 11/2001 | Tsugita et al. |
| 2001/0044632 A1 | 11/2001 | Daniel et al. |
| 2001/0044634 A1 | 11/2001 | Don Michael et al. |
| 2001/0053921 A1 | 12/2001 | Jang |
| 2002/0002384 A1 | 1/2002 | Gilson et al. |
| 2002/0004667 A1 | 1/2002 | Adams et al. |
| 2002/0016564 A1 | 2/2002 | Courtney et al. |
| 2002/0016609 A1 | 2/2002 | Wensel et al. |
| 2002/0022858 A1 | 2/2002 | Demond et al. |
| 2002/0022859 A1 | 2/2002 | Hogendijk |
| 2002/0026211 A1 | 2/2002 | Khosravi et al. |
| 2002/0026212 A1 | 2/2002 | Wholey et al. |
| 2002/0026213 A1 | 2/2002 | Gilson et al. |
| 2002/0032460 A1 | 3/2002 | Kusleika et al. |
| 2002/0032461 A1 | 3/2002 | Marshall |
| 2002/0042626 A1 | 4/2002 | Hanson et al. |
| 2002/0042627 A1 | 4/2002 | Brady et al. |
| 2002/0045915 A1 | 4/2002 | Balceta et al. |
| 2002/0045916 A1 | 4/2002 | Gray et al. |
| 2002/0045918 A1 | 4/2002 | Suon et al. |
| 2002/0049452 A1 | 4/2002 | Kurz et al. |
| 2002/0049468 A1 | 4/2002 | Streeter et al. |
| 2002/0052627 A1 | 5/2002 | Boylan et al. |
| 2002/0058904 A1 | 5/2002 | Boock et al. |
| 2002/0058911 A1 | 5/2002 | Gilson et al. |
| 2002/0058963 A1 | 5/2002 | Vale et al. |
| 2002/0058964 A1 | 5/2002 | Addis |
| 2002/0062133 A1 | 5/2002 | Gilson et al. |
| 2002/0062134 A1 | 5/2002 | Barbut et al. |
| 2002/0062135 A1 | 5/2002 | Mazzocchi et al. |
| 2002/0065507 A1 | 5/2002 | Zadno-Azizi |
| 2002/0068954 A1 | 6/2002 | Foster |
| 2002/0068955 A1 | 6/2002 | Khosravi |
| 2002/0072764 A1 | 6/2002 | Sepetka et al. |
| 2002/0072765 A1 | 6/2002 | Mazzocchi et al. |
| 2002/0077596 A1 | 6/2002 | McKenzie et al. |
| 2002/0082558 A1 | 6/2002 | Samson et al. |
| 2002/0082639 A1 | 6/2002 | Broome et al. |
| 2002/0087187 A1 | 7/2002 | Mazzocchi et al. |
| 2002/0090389 A1 | 7/2002 | Humes et al. |
| 2002/0091407 A1 | 7/2002 | Zadno-Azizi et al. |
| 2002/0091408 A1 | 7/2002 | Sutton et al. |
| 2002/0091409 A1 | 7/2002 | Sutton et al. |
| 2002/0095170 A1 | 7/2002 | Krolik et al. |
| 2002/0095171 A1 | 7/2002 | Belef |
| 2002/0095172 A1 | 7/2002 | Mazzocchi et al. |
| 2002/0095173 A1 | 7/2002 | Mazzocchi et al. |
| 2002/0095174 A1 | 7/2002 | Tsugita et al. |
| 2002/0099407 A1 | 7/2002 | Becker et al. |
| 2002/0103501 A1 | 8/2002 | Diaz et al. |
| 2002/0107541 A1 | 8/2002 | Vale et al. |
| 2002/0111647 A1 | 8/2002 | Khairkhahan et al. |

(56) References Cited

U.S. PATENT DOCUMENTS

| | | |
|---|---|---|
| 2002/0111648 A1 | 8/2002 | Kusleika et al. |
| 2002/0111649 A1 | 8/2002 | Russo et al. |
| 2002/0116024 A1 | 8/2002 | Goldberg et al. |
| 2002/0120226 A1 | 8/2002 | Beck |
| 2002/0120286 A1 | 8/2002 | DoBrava et al. |
| 2002/0120287 A1 | 8/2002 | Huter |
| 2002/0123720 A1 | 9/2002 | Kusleika et al. |
| 2002/0123755 A1 | 9/2002 | Lowe et al. |
| 2002/0123759 A1 | 9/2002 | Amplatz |
| 2002/0123766 A1 | 9/2002 | Seguin et al. |
| 2002/0128679 A1 | 9/2002 | Turovskiy et al. |
| 2002/0128680 A1 | 9/2002 | Pavlovic |
| 2002/0128681 A1 | 9/2002 | Broome et al. |
| 2002/0133191 A1 | 9/2002 | Khosravi et al. |
| 2002/0133192 A1 | 9/2002 | Kusleika et al. |
| 2002/0138094 A1 | 9/2002 | Borillo et al. |
| 2002/0138095 A1 | 9/2002 | Mazzocchi et al. |
| 2002/0138096 A1 | 9/2002 | Hieshima |
| 2002/0138097 A1 | 9/2002 | Ostrovsky et al. |
| 2002/0143360 A1 | 10/2002 | Douk et al. |
| 2002/0143361 A1 | 10/2002 | Douk et al. |
| 2002/0143362 A1 | 10/2002 | Macoviak et al. |
| 2002/0151927 A1 | 10/2002 | Douk et al. |
| 2002/0151928 A1 | 10/2002 | Leslie et al. |
| 2002/0156520 A1 | 10/2002 | Boylan et al. |
| 2002/0161389 A1 | 10/2002 | Boyle et al. |
| 2002/0161390 A1 | 10/2002 | Mouw |
| 2002/0161391 A1 | 10/2002 | Murphy et al. |
| 2002/0161392 A1 | 10/2002 | Dubrul |
| 2002/0161393 A1 | 10/2002 | Demond et al. |
| 2002/0161394 A1 | 10/2002 | Macoviak et al. |
| 2002/0161395 A1 | 10/2002 | Douk et al. |
| 2002/0161396 A1 | 10/2002 | Jang et al. |
| 2002/0165557 A1 | 11/2002 | McAlister |
| 2002/0165573 A1 | 11/2002 | Barbut |
| 2002/0165576 A1 | 11/2002 | Boyle et al. |
| 2002/0169472 A1 | 11/2002 | Douk et al. |
| 2002/0169474 A1 | 11/2002 | Kusleika et al. |
| 2002/0173815 A1 | 11/2002 | Hogendijk et al. |
| 2002/0173819 A1 | 11/2002 | Leeflang et al. |
| 2002/0177872 A1 | 11/2002 | Papp et al. |
| 2002/0183781 A1 | 12/2002 | Casey et al. |
| 2002/0183782 A1 | 12/2002 | Tsugita et al. |
| 2002/0183783 A1 | 12/2002 | Shadduck |
| 2002/0188313 A1 | 12/2002 | Johnson et al. |
| 2002/0188314 A1 | 12/2002 | Anderson et al. |
| 2002/0193824 A1 | 12/2002 | Boylan et al. |
| 2002/0193825 A1 | 12/2002 | McGuckin et al. |
| 2002/0193826 A1 | 12/2002 | McGuckin et al. |
| 2002/0193827 A1 | 12/2002 | McGuckin et al. |
| 2002/0193828 A1 | 12/2002 | Griffin et al. |
| 2002/0198561 A1 | 12/2002 | Amplatz |
| 2003/0004536 A1 | 1/2003 | Boylan et al. |
| 2003/0004538 A1 | 1/2003 | Secrest et al. |
| 2003/0004539 A1 | 1/2003 | Linder et al. |
| 2003/0004540 A1 | 1/2003 | Linder et al. |
| 2003/0004541 A1 | 1/2003 | Linder et al. |
| 2003/0004542 A1 | 1/2003 | Wensel et al. |
| 2003/0009146 A1 | 1/2003 | Muni et al. |
| 2003/0009189 A1 | 1/2003 | Gilson et al. |
| 2003/0009190 A1 | 1/2003 | Kletschka et al. |
| 2003/0009191 A1 | 1/2003 | Wensel et al. |
| 2003/0014072 A1 | 1/2003 | Wensel et al. |
| 2003/0018354 A1 | 1/2003 | Roth et al. |
| 2003/0018355 A1 | 1/2003 | Goto et al. |
| 2003/0023263 A1 | 1/2003 | Krolik et al. |
| 2003/0023264 A1 | 1/2003 | Dieck et al. |
| 2003/0023265 A1 | 1/2003 | Forber |
| 2003/0032976 A1 | 2/2003 | Boucck |
| 2003/0032977 A1 | 2/2003 | Brady |
| 2003/0040772 A1 | 2/2003 | Hyodoh et al. |
| 2003/0045897 A1 | 3/2003 | Huter et al. |
| 2003/0045898 A1 | 3/2003 | Harrison et al. |
| 2003/0050662 A1 | 3/2003 | Don Michael |
| 2003/0055452 A1 | 3/2003 | Joergensen et al. |
| 2003/0055480 A1 | 3/2003 | Fischell et al. |
| 2003/0060843 A1 | 3/2003 | Boucher |
| 2003/0060844 A1* | 3/2003 | Borillo et al. .............. 606/200 |
| 2003/0065354 A1 | 4/2003 | Boyle et al. |
| 2003/0065355 A1 | 4/2003 | Weber |
| 2003/0065356 A1 | 4/2003 | Tsugita et al. |
| 2003/0069596 A1 | 4/2003 | Eskuri |
| 2003/0073979 A1 | 4/2003 | Naimark et al. |
| 2003/0074019 A1 | 4/2003 | Gray et al. |
| 2003/0078614 A1 | 4/2003 | Salahieh et al. |
| 2003/0083692 A1 | 5/2003 | Vrba et al. |
| 2003/0083693 A1 | 5/2003 | Daniel et al. |
| 2003/0088211 A1 | 5/2003 | Anderson et al. |
| 2003/0088266 A1 | 5/2003 | Bowlin |
| 2003/0093110 A1 | 5/2003 | Vale |
| 2003/0093112 A1 | 5/2003 | Addis |
| 2003/0097094 A1 | 5/2003 | Ouriel et al. |
| 2003/0097145 A1 | 5/2003 | Goldberg et al. |
| 2003/0100917 A1 | 5/2003 | Boyle et al. |
| 2003/0100918 A1 | 5/2003 | Duane |
| 2003/0100919 A1 | 5/2003 | Hopkins et al. |
| 2003/0105472 A1 | 6/2003 | McAlister |
| 2003/0105484 A1 | 6/2003 | Boyle et al. |
| 2003/0105486 A1 | 6/2003 | Murphy et al. |
| 2003/0109824 A1 | 6/2003 | Anderson et al. |
| 2003/0109897 A1 | 6/2003 | Walak et al. |
| 2003/0114879 A1 | 6/2003 | Euteneuer et al. |
| 2003/0114880 A1 | 6/2003 | Hansen et al. |
| 2003/0120303 A1 | 6/2003 | Boyle et al. |
| 2003/0120304 A1 | 6/2003 | Kaganov et al. |
| 2003/0125764 A1 | 7/2003 | Brady et al. |
| 2003/0125765 A1 | 7/2003 | Blackledge et al. |
| 2003/0130680 A1 | 7/2003 | Russell |
| 2003/0130681 A1 | 7/2003 | Ungs |
| 2003/0130682 A1 | 7/2003 | Broome et al. |
| 2003/0130684 A1 | 7/2003 | Brady et al. |
| 2003/0130685 A1 | 7/2003 | Daniel et al. |
| 2003/0130686 A1 | 7/2003 | Daniel et al. |
| 2003/0130687 A1 | 7/2003 | Daniel et al. |
| 2003/0130688 A1 | 7/2003 | Daniel et al. |
| 2003/0135232 A1 | 7/2003 | Douk et al. |
| 2003/0135233 A1 | 7/2003 | Bates et al. |
| 2003/0139764 A1 | 7/2003 | Levinson et al. |
| 2003/0139765 A1 | 7/2003 | Patel et al. |
| 2003/0144685 A1 | 7/2003 | Boyle et al. |
| 2003/0144686 A1 | 7/2003 | Martinez et al. |
| 2003/0144687 A1 | 7/2003 | Brady et al. |
| 2003/0144688 A1 | 7/2003 | Brady et al. |
| 2003/0144689 A1 | 7/2003 | Brady et al. |
| 2003/0150821 A1 | 8/2003 | Bates et al. |
| 2003/0153935 A1 | 8/2003 | Mialhe |
| 2003/0153942 A1 | 8/2003 | Wang et al. |
| 2003/0153943 A1 | 8/2003 | Michael et al. |
| 2003/0153944 A1 | 8/2003 | Phung et al. |
| 2003/0153945 A1 | 8/2003 | Patel et al. |
| 2003/0158518 A1 | 8/2003 | Schonholz et al. |
| 2003/0158574 A1 | 8/2003 | Esch et al. |
| 2003/0158575 A1 | 8/2003 | Boylan et al. |
| 2003/0163158 A1 | 8/2003 | White |
| 2003/0163159 A1 | 8/2003 | Patel et al. |
| 2003/0167068 A1 | 9/2003 | Amplatz |
| 2003/0167069 A1 | 9/2003 | Gonzales et al. |
| 2003/0171769 A1 | 9/2003 | Barbut |
| 2003/0171770 A1 | 9/2003 | Kusleika et al. |
| 2003/0171771 A1 | 9/2003 | Anderson et al. |
| 2003/0171772 A1 | 9/2003 | Amplatz |
| 2003/0171803 A1 | 9/2003 | Shimon |
| 2003/0176884 A1 | 9/2003 | Berrada et al. |
| 2003/0176885 A1 | 9/2003 | Broome et al. |
| 2003/0176886 A1 | 9/2003 | Wholey et al. |
| 2003/0176887 A1 | 9/2003 | Petersen |
| 2003/0176888 A1 | 9/2003 | O'Connell |
| 2003/0176889 A1 | 9/2003 | Boyle et al. |
| 2003/0181942 A1 | 9/2003 | Sutton et al. |
| 2003/0181943 A1 | 9/2003 | Daniel et al. |
| 2003/0187474 A1 | 10/2003 | Keegan et al. |
| 2003/0187475 A1 | 10/2003 | Tsugita et al. |
| 2003/0187495 A1 | 10/2003 | Cully et al. |
| 2003/0191492 A1 | 10/2003 | Gellman et al. |

(56) References Cited

U.S. PATENT DOCUMENTS

| | | |
|---|---|---|
| 2003/0191493 A1 | 10/2003 | Epstein et al. |
| 2003/0195554 A1 | 10/2003 | Shen et al. |
| 2003/0195555 A1 | 10/2003 | Khairkhahan et al. |
| 2003/0199819 A1 | 10/2003 | Beck |
| 2003/0199917 A1 | 10/2003 | Knudson et al. |
| 2003/0199918 A1 | 10/2003 | Patel et al. |
| 2003/0199919 A1 | 10/2003 | Palmer et al. |
| 2003/0199920 A1 | 10/2003 | Boylan et al. |
| 2003/0199921 A1 | 10/2003 | Palmer et al. |
| 2003/0204168 A1 | 10/2003 | Bosma et al. |
| 2003/0204202 A1 | 10/2003 | Palmer et al. |
| 2003/0204203 A1 | 10/2003 | Khairkhahan et al. |
| 2003/0208222 A1 | 11/2003 | Zadno-Azizi |
| 2003/0208224 A1 | 11/2003 | Broome |
| 2003/0208225 A1 | 11/2003 | Goll et al. |
| 2003/0208226 A1 | 11/2003 | Bruckheimer et al. |
| 2003/0208227 A1 | 11/2003 | Thomas |
| 2003/0208228 A1 | 11/2003 | Gilson et al. |
| 2003/0208229 A1 | 11/2003 | Kletschka |
| 2003/0208253 A1 | 11/2003 | Beyer et al. |
| 2003/0212428 A1 | 11/2003 | Richter |
| 2003/0212429 A1 | 11/2003 | Keegan et al. |
| 2003/0212432 A1 | 11/2003 | Khairkhahan et al. |
| 2003/0212433 A1 | 11/2003 | Ambrisco et al. |
| 2003/0216774 A1 | 11/2003 | Larson |
| 2003/0220665 A1 | 11/2003 | Eskuri et al. |
| 2003/0220667 A1 | 11/2003 | Van der Burg et al. |
| 2003/0225435 A1 | 12/2003 | Hunter et al. |
| 2003/0229374 A1 | 12/2003 | Brady et al. |
| 2003/0233117 A1 | 12/2003 | Adams et al. |
| 2004/0006364 A1 | 1/2004 | Ladd |
| 2004/0006370 A1 | 1/2004 | Tsugita |
| 2004/0039412 A1 | 2/2004 | Isshiki et al. |
| 2004/0059372 A1 | 3/2004 | Tsugita |
| 2004/0064067 A1 | 4/2004 | Ward |
| 2004/0068271 A1 | 4/2004 | McAlister |
| 2004/0078044 A1 | 4/2004 | Kear |
| 2004/0082962 A1 | 4/2004 | Demarais et al. |
| 2004/0093016 A1 | 5/2004 | Root et al. |
| 2004/0098022 A1 | 5/2004 | Barone |
| 2004/0098033 A1 | 5/2004 | Leeflang et al. |
| 2004/0098112 A1 | 5/2004 | DiMatteo et al. |
| 2004/0106944 A1 | 6/2004 | Daniel et al. |
| 2004/0116831 A1 | 6/2004 | Vrba |
| 2004/0133232 A1 | 7/2004 | Rosenbluth et al. |
| 2004/0158278 A1 | 8/2004 | Becker et al. |
| 2004/0164030 A1 | 8/2004 | Lowe et al. |
| 2004/0167567 A1 | 8/2004 | Cano et al. |
| 2004/0176794 A1 | 9/2004 | Khosravi |
| 2004/0176833 A1 | 9/2004 | Pavcnik et al. |
| 2004/0236369 A1 | 11/2004 | Dubrul |
| 2005/0038468 A1 | 2/2005 | Panetta et al. |
| 2006/0100544 A1 | 5/2006 | Ayala et al. |
| 2006/0100545 A1 | 5/2006 | Ayala et al. |

\* cited by examiner

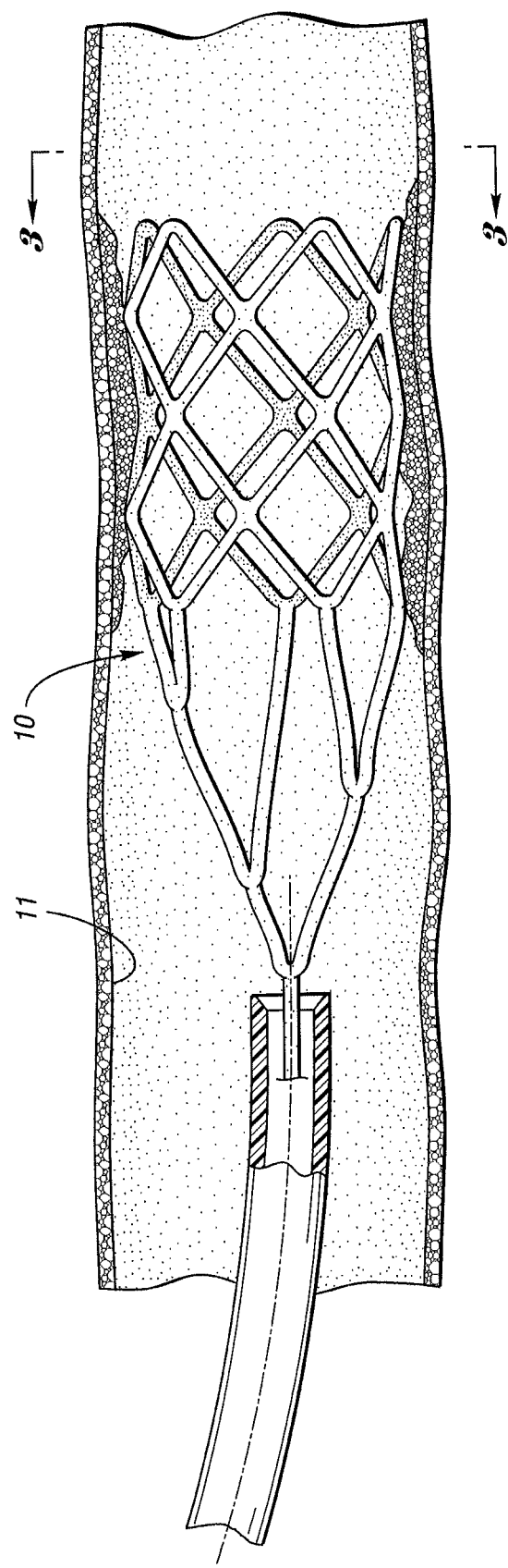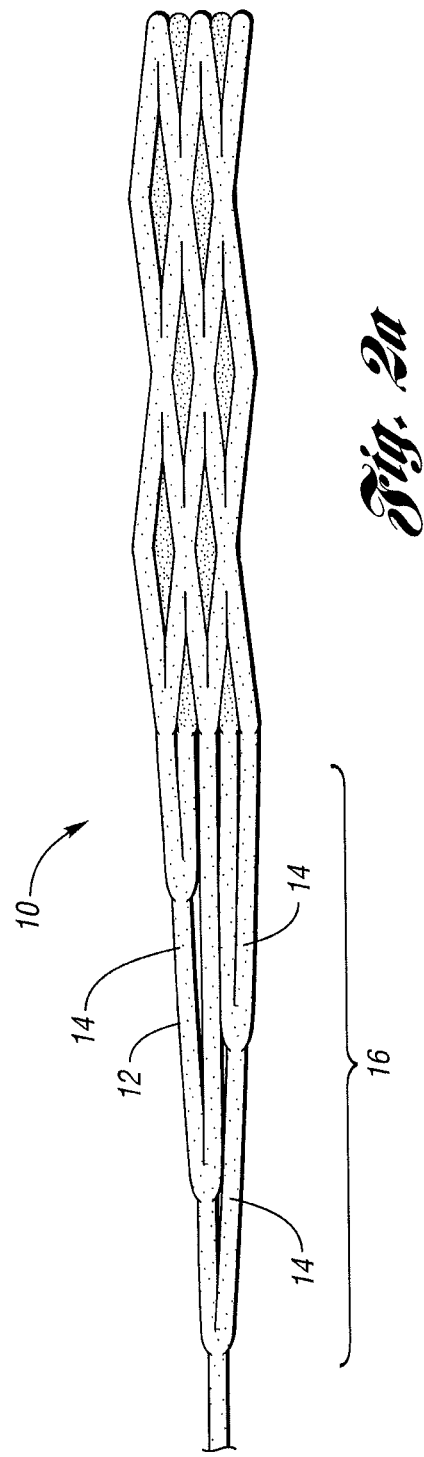
Fig. 1
Fig. 2a

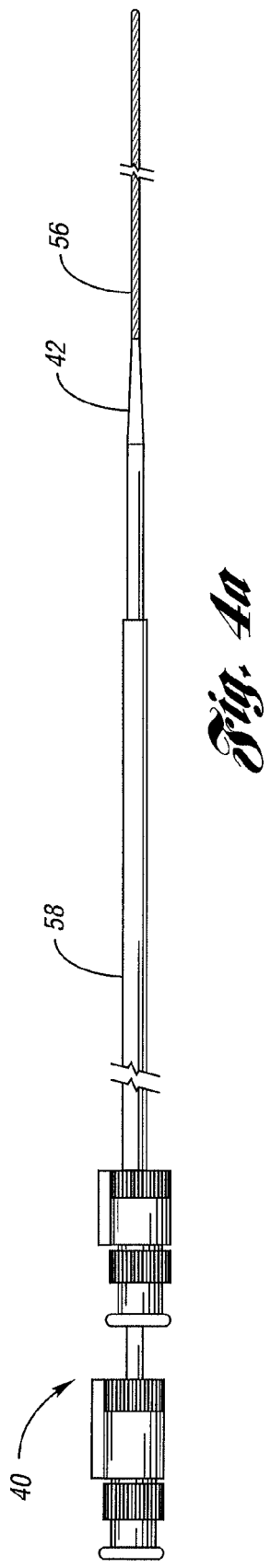
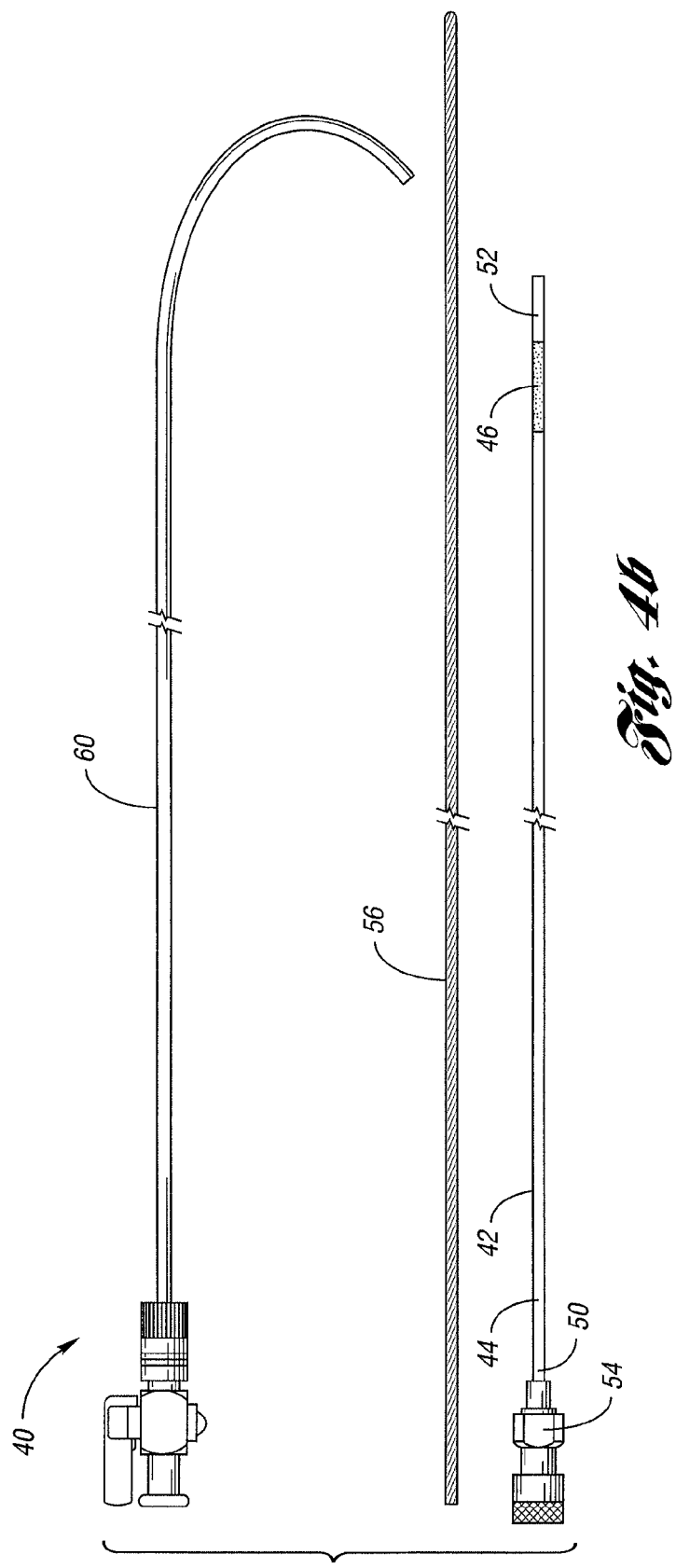

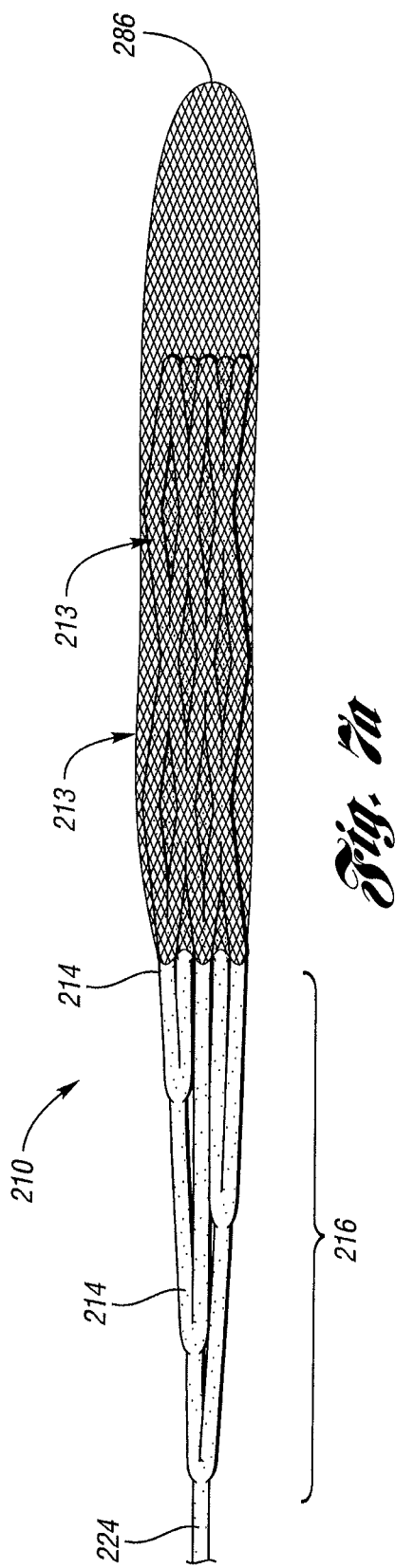
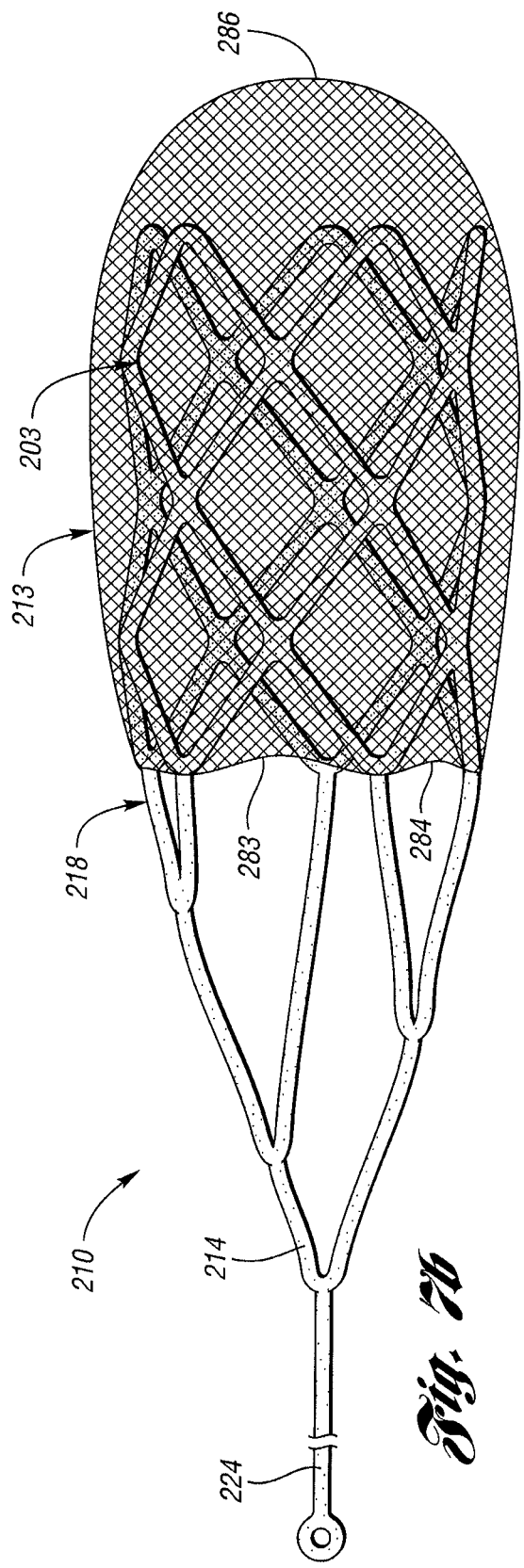

RETRIEVABLE DEVICE HAVING A RETICULATION PORTION WITH STAGGERED STRUTS

CROSS-REFERENCE TO RELATED APPLICATION

This application is a Continuation of U.S. application Ser. No. 11/455,421, filed on Jun. 19, 2006 and issued as U.S. Pat. No. 8,109,962, and claims the benefit of U.S. Provisional Application No. 60/692,317, filed on Jun. 20, 2005, entitled "Retrievable Device Having A Reticulation Portion With Staggered Struts," the entire contents of which are incorporated herein by reference.

BACKGROUND OF THE INVENTION

The present invention relates to medical devices. More particularly, the present invention relates to retrievable devices, methods for treating a stenotic lesion in a body vessel, and methods for capturing emboli during treatment of a stenotic lesion within a body vessel.

Treatments for a stenotic lesion are continuously being improved. One example is the treatment for carotid artery stenosis. Generally, carotid artery stenosis is the narrowing of the carotid arteries, the main arteries in the neck that supply blood to the brain. Carotid artery stenosis (also called carotid artery disease) is a relatively high risk factor for ischemic stroke. The narrowing is usually caused by plaque build-up in the carotid artery. Plaque forms when cholesterol, fat and other substances form in the inner lining of an artery. This formation process is called atherosclerosis.

Depending on the degree of stenosis and the patient's overall condition, carotid artery stenosis has been treated with surgery. The procedure (with its inherent risks) is called carotid endarterectomy, which removes the plaque from the arterial walls. Carotid endarterectomy has proven to benefit patients with arteries substantially narrowed, e.g., by about 70% or more. For people with less narrowed arteries, e.g., less than about 50%, an anti-clotting drug may be prescribed to reduce the risk of ischemic stroke. Examples of these drugs are anti-platelet agents and anticoagulants.

Carotid angioplasty is a more recently developed treatment for carotid artery stenosis. This treatment uses balloons and/or stents to open a narrowed artery. Carotid angioplasty is a procedure that can be performed via a standard percutaneous transfemoral approach with the patient anesthetized using light intravenous sedation. At the stenosis area, an angioplasty balloon is delivered to predilate the stenosis in preparation for stent placement. The balloon is then removed and exchanged via catheter for a stent delivery device. Once in position, a stent is deployed across the stenotic area. If needed, an additional balloon can be placed inside the deployed stent for post-dilation to make sure the struts of the stent are pressed firmly against the inner surface of the vessel wall.

Currently, stents used for treatment of a stenosis are typically permanent devices when deployed in a body vessel. In many situations, when a stenosis condition has passed, the deployed stent can not be removed from the patient.

Thus, there is a need to provide a retrievable device, e.g., a stent, for treatment of a stenosis in a body vessel.

BRIEF SUMMARY OF THE INVENTION

The present invention generally provides a retrievable device for treatment of a stenotic lesion in a body vessel, allowing for removal of the device after a stenosis condition has passed in the body vessel. Embodiments of the present invention provide a device for treating a stenotic lesion of a blood vessel while allowing removal of the device after the stenosis condition has passed.

In one embodiment, the present invention provides a retrievable device for treatment of a stenotic lesion in a body vessel. The device comprises a reticulation portion having a deployed state and a collapsed state. The reticulation portion includes a plurality of struts connected together in a singly staggered configuration distally along a longitudinal axis. The plurality of struts of the reticulation portion is configured to fold along the longitudinal axis defining a collapsed state of the device for retrieval. The device further comprises an expandable body distally extending from the reticulation portion along on outer diameter for treatment of the stenotic lesion. The expandable body is configured to expand in the deployed state and collapsed in the collapsed state of the reticulation portion for retrieval. The device further comprises a retrieval stem extending proximally from the reticulation portion for retrieval of the device in the collapsed state.

In another embodiment, the present invention provides for an angioplasty assembly having a retrievable stent for treating a stenotic lesion in a body vessel. The assembly comprises an outer catheter including a tubular body having a distal end. The assembly further comprises a retrievable stent coaxially disposable within the tubular body of the outer catheter and deployable through the distal end thereof for treatment of the stenotic lesion in the body vessel. In this embodiment, the stent comprises the reticulation portion, the expandable body, and the retrieval stem.

In another example, the present invention provides a method for treating a stenotic lesion in a body vessel. The method comprises providing the retrievable stent deployed from the outer catheter at the stenotic lesion in the body and singly folding each of the struts about each pivotal joint to collapse the reticulation portion in the collapsed state. The method further comprises retracting a stent in the outer catheter to retrieve the stent from the body vessel.

Further objects, features, and advantages of the present invention will become apparent from consideration of the following description and the appended claims when taken in connection with the accompanying drawings.

BRIEF DESCRIPTION OF THE DRAWINGS

FIG. 1 is an environmental view of a retrievable device for treatment of a stenotic lesion in a body vessel in accordance with one embodiment of the present invention;

FIG. 2a is a side view of the retrievable device in a collapsed state;

FIG. 4a a side view of a delivery assembly for a retrievable stent for treatment of a stenotic lesion in accordance with one embodiment of the present invention;

FIG. 4b is an exploded view of the assembly of FIG. 4a;

FIG. 7a is a side view of the retrieval device of FIG. 6 in a collapsed state; and FIG. 7b is a side view of the retrieval device of FIG. 6 in an expanded state.

DETAILED DESCRIPTION OF THE INVENTION

Figure 2B:
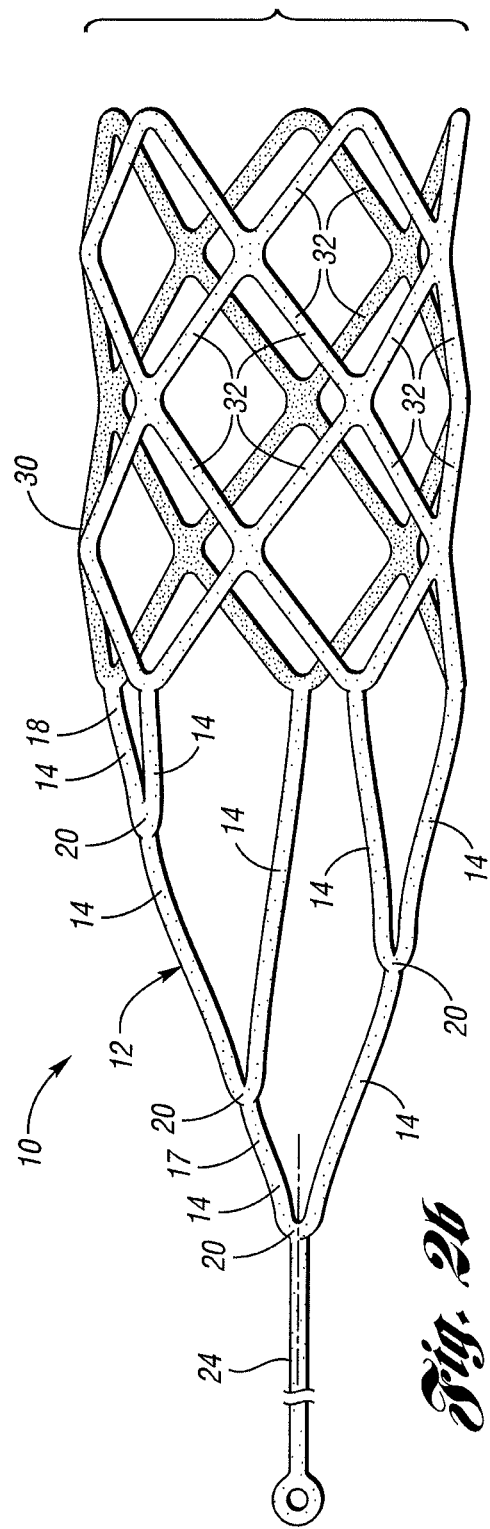
FIG. 2b is a side view of the retrievable device in an expanded state.

The present invention generally provides a retrievable device that is removable from a body vessel after a stenosis condition has passed or after treatment of a stenotic lesion. Embodiments of the present invention generally provide a device, e.g., a retrievable stent, comprising a reticulation portion including a plurality of struts connected together in a singly staggered configuration distally along a longitudinal axis. The singly staggered configuration allows for relatively easy retrieval of the device. Moreover, the device comprises an expandable body that distally extends from the reticulation portion along an outer diameter for treatment of the stenotic lesion.

FIG. 1 illustrates a retrievable device 10 for treatment of a stenotic lesion in a body vessel 11 in accordance with one embodiment of the present invention. As shown, in FIGS. 1 through 2b, the device 10 comprises a reticulation portion 12 having an expanded state and a collapsed state. The reticulation portion 12 includes a plurality of struts 14 connected together in a singly staggered configuration 16 distally along a longitudinal axis A. The plurality of struts 14 of the reticulation portion 12 is configured to fold along the longitudinal axis, defining the collapsed state of the device 10 for retrieval.

In this embodiment, the reticulation portion 12 extends along an outer diameter 22 when in the expanded state. As shown, the singly staggered configuration 16 of the plurality of struts 14 distally extends from a proximal portion 17 of the reticulation portion 12 along the longitudinal axis A to a distal portion 18 thereof. In the expanded state, each of the struts 14 of the reticulation portion 12 is configured to fold singly in pairs along the longitudinal axis A to the collapsed state. As will be described in greater detail below, the singly staggered configuration 16 allows the device 10 to be relatively easily collapsed and retrieved when deployed at a stenotic area within the vasculature of a patient.

Figure 2C:
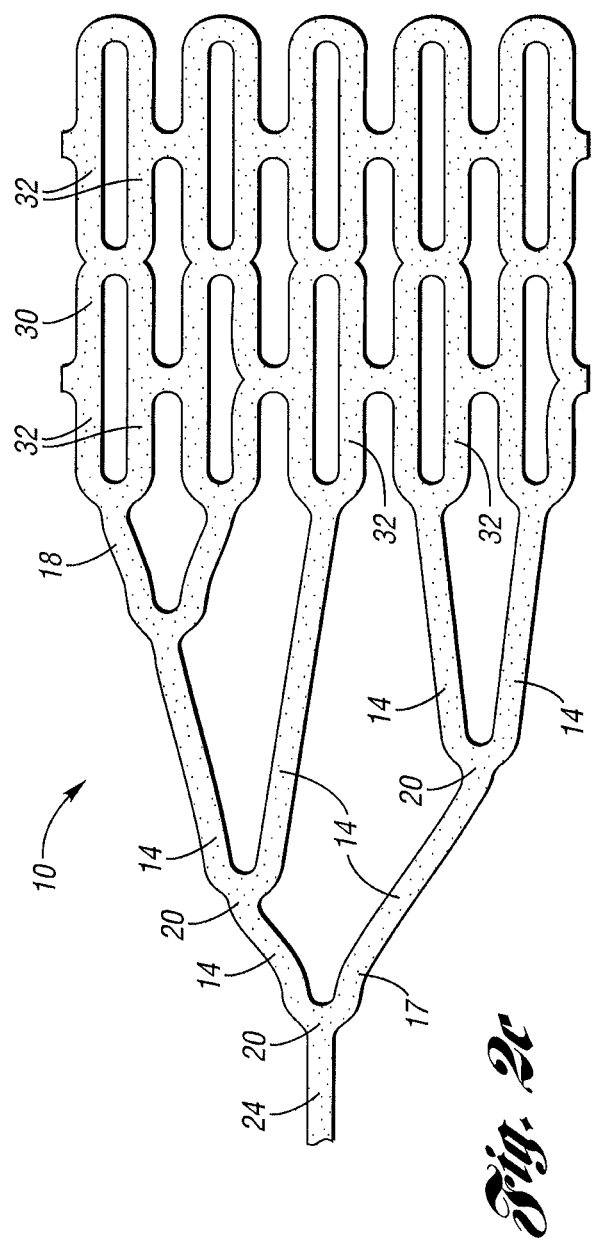
FIG. 2c is a plan view of the retrievable device.

As shown in FIGS. 2b and 2c, the reticulation portion 12 is formed so that each strut 14 is singly connected to another strut 14 in pairs relative to the longitudinal axis. Preferably, the struts 14 are connected together at pivotal joints 20 along the reticulation portion 12. In this embodiment, one pair of struts 14 is connected to one pivotal joint 20. Each of the pivotal joints 20 is configured to allow a pair of struts 14 to singly fold distally along the longitudinal axis. As shown, a pair of struts 14 distally extends from a single pivotal joint 20 at the proximal stem 24. In this embodiment, two struts 14 are disposed on and extend from the proximal stem 24 and up to ten struts 14 may be formed at the distal portion 18 of the reticulation portion 12. When each of the pairs of struts 14 is folded at the pivotal joints 20, the reticulation portion 12 is collapsed to its collapsed state for delivery or retrieval of the device 10. This feature allows a catheter or sheath to circumferentially ride over each pivotal joint 20 for relatively easy collapse and retrieval of the device 10.

Figure 3:
FIG. 3 is an end view of the retrievable device.

The reticulation portion 12 distally extends from the proximal portion 17 to the distal portion 18 along the outer diameter 22. Preferably, the reticulation portion 12 extends substantially constant along the outer diameter 22 when in the expanded state. As shown in FIGS. 2b and 3, the reticulation portion 12 extends along the outer diameter 22 and maintains substantially the same or constant diameter therealong from the proximal portion 17 to the distal portion 18 of the reticulation portion 12. In the expanded state, the reticulation portion 12 avoids placement at or near the center of the body vessel in which it is deployed. Preferably, the number of struts 14 and pivotal joints 20 on the reticulation portion 12 distally increases in a singly staggered configuration 16 along the longitudinal axis.

As mentioned above, FIGS. 2b and 3 illustrate that the device 10 maintains a substantially constant outer diameter 22 relative to the longitudinal axis. As shown, the outer diameter 22 of the device 10 is substantially constant. In this embodiment, the term "constant" outer diameter 22 or "substantially constant" outer diameter 22 of the device 10 means that the device 10 extends along the longitudinal axis A having about the same outer diameter. For instance, if the outer diameter 22 of the device 10 at the proximal portion 17 is about 5 millimeters (mm), then the outer diameter 22 of the portion along the remainder of the device 10 is also about 5 mm. Thus, the outer diameter 22 of the reticulation portion 12 is substantially constant distally extending therealong to the expandable body 30.

FIG. 2a illustrates the device 10 in its collapsed or closed state in accordance with one embodiment of the present invention. As shown, the device 10 has a reduced diameter, occupying a cross-sectional profile less than the outer diameter 22 of the device 10 in the expanded state. The pivotal joints 20 of the reticulation portion 12 singly increase distally along the longitudinal axis of the device 10. Thus, the reticulation portion 12 in the collapsed state distally increases in width in a singly staggered configuration 16. For example, the reticulation portion 12 in the collapsed configuration includes pairs of folded struts 14 singly staggered at their respective pivotal joints 20 which distally increase in number, thereby distally increasing the width as the reticulation portion 12 distally extends.

FIGS. 2a-2c further depict the device 10 having a proximal stem 24. As shown, the proximal stem 24 proximally extends from the proximal portion 17 of the reticulation portion 12 along the outer diameter 22 thereof. Thus, the proximal stem 24 is positioned off-centered to allow maximum blood flow through the device 10 when deployed in a body vessel. The proximal stem 24 may proximally extend from the reticulation portion 12 and take on any suitable shape along the outer diameter 22 of the reticulation portion 12. For example, the proximal stem 24 may take on a shape of an elongated member that may be disposed within an outer catheter 60 for placement within a body vessel for stenosis treatment. However, it is understood that the proximal stem 24 may take on other shapes without falling beyond the scope or spirit of the present invention.

As mentioned, the proximal stem 24 extends in alignment with the outer diameter 22 of the reticulation portion 12 relative to a radial axis of the device 10. This allows for more effective filtering and lessens the risk of blood flow issues within the vasculature during angioplasty, while maintaining a relatively easy way for delivery and retrieval. However, the proximal stem 24 may be configured as desired to extend circumferentially within, in non-alignment with, the outer diameter 22 of the device 10.

In this embodiment, the device 10 further includes an expandable body 30 distally extending from the reticulation portion 12 along the outer diameter 22 for treatment of the stenotic lesion. The expandable body 30 is configured to open in the expanded state for angioplasty and close in the collapsed state for delivery and retrieval. The expandable body 30 may be configured in any suitable manner to expand and collapse. For example, the expandable body 30 may comprise a plurality of branches 32 connected together as shown in FIGS. 2b and 2c. In this embodiment, the plurality of branches 32 is configured to fold along the longitudinal axis as the struts 14 of the reticulation portion 12 fold therealong. The expandable body 30 may be made of the same material as the reticulation portion 12, e.g., shape memory material.

The device 10 may be comprised of any suitable material such as a superelastic material, stainless steel wire, cobalt-chromium-nickel-molybdenum-iron alloy, or cobalt-chrome alloy. It is understood that the device 10 may be formed of any other suitable material that will result in a self-opening or self-expanding device 10, such as shape memory material. Shape memory materials or alloys have the desirable property of becoming rigid, i.e., returning to a remembered state, when heated above a transition temperature. A shape memory alloy suitable for the present invention is Ni—Ti available under the more commonly known name Nitinol. When this material is heated above the transition temperature, the material undergoes a phase transformation from martensite to austenic, such that material returns to its remembered state. The transition temperature is dependent on the relative proportions of the alloying elements Ni and Ti and the optional inclusion of alloying additives.

In one embodiment, the device 10 is made from Nitinol with a transition temperature that is slightly below normal body temperature of humans, which is about 98.6° F. Thus, when the device 10 is deployed in a body vessel and exposed to normal body temperature, the alloy of the device 10 will transform to austenite, that is, the remembered state, which for one embodiment of the present invention is the expanded configuration when the device 10 is deployed in the body vessel. To remove the device 10, the device 10 is cooled to transform the material to martensite which is more ductile than austenite, making the device 10 more malleable. As such, the device 10 can be more easily collapsed and pulled into a lumen of a catheter for removal.

In another embodiment, the device 10 is made from Nitinol with a transition temperature that is above normal body temperature of humans, which is about 98.6° F. Thus, when the device 10 is deployed in a body vessel and exposed to normal body temperature, the device 10 is in the martensitic state so that the device 10 is sufficiently ductile to bend or form into a desired shape, which for the present invention is an expanded configuration. To remove the device 10, the device 10 is heated to transform the alloy to austenite so that the device 10 becomes rigid and returns to a remembered state, which for the device 10 in a collapsed configuration.

FIGS. 4a-4b depict an assembly 40 which implements the device 10 for treating a stenotic lesion of a body vessel in accordance with one embodiment of the present invention. As shown, the assembly 40 includes a balloon catheter 42 having a tubular body 44 and an expandable balloon 46 disposed thereabout. The expandable balloon 46 is preferably attached to and in fluid communication with the tubular body 44 for angioplasty at the stenotic lesion. The device 10 is configured to be disposed about the expandable balloon 46 for deployment at the stenotic lesion. The device 10 may be placed about the angioplasty balloon of the angioplasty catheter prior to insertion into the vasculature.

Generally, the balloon catheter 42 has a proximal end 50, a distal end 52, and a plastic adapter or hub 54 to receive the assembly 40 to be advanced therethrough. The hub 54 is in fluid communication with the balloon for fluid to be passed therethrough for inflation and deflation of the balloon during angioplasty. In one embodiment, the balloon catheter 42 may include an outer lumen and an inner lumen. The outer lumen is preferably in fluid communication with the expandable balloon 46 for inflating and deflating the balloon. The inner lumen is formed therethrough for percutaneous guidance through the body vessel. The balloon catheter 42 is preferably made of a soft, flexible material such as a silicone or any other suitable material.

The size of the expandable balloon 46 may vary. For example, the balloon size may range between about 2 and 10 millimeters in diameter. The expandable balloon 46 has distal and proximal portions 17. The expandable balloon 46 may be made of any suitable material such as low density polymer material such as polyvinyl chloride.

The assembly 40 further includes a wire guide 56 which via an introducer sheath 58 (discussed in greater detail below) is percutaneously inserted to provide a path for the balloon catheter 42 within the vasculature of a patient. The balloon catheter 42 is configured to be disposed about the wire guide 56 for percutaneous guidance through the vasculature. The size of the wire guide 56 is based on the inside diameter of the introducer sheath 58.

As mentioned above, the assembly 40 further includes a polytetrafluoroethylene (PTFE) introducer sheath 58 for percutaneously introducing the wire guide 56 and the balloon catheter 42 in vasculature. Of course, any other suitable material may be used without falling beyond the scope or spirit of the present invention. The introducer sheath 58 is percutaneously inserted into the vasculature of the patient. The sheath 58 may have a size of about 4-French to 8-French and allows the balloon catheter 42 to be inserted therethrough to the deployment location in the body vessel. In one embodiment, the sheath receives the balloon catheter 42 and the device 10, and provides stability thereto at the deployment location.

The assembly 40 may further include an outer catheter 60 disposed co-axially about the balloon catheter 42 within the introducer sheath 58. As shown, the outer catheter 60 is preferably configured to house the balloon catheter 42 and the device 10 during delivery and retrieval thereof to and from the stenotic lesion. The outer catheter 60 is preferably advanced with the balloon catheter 42 and the device 10 to the deployment location. When the distal end 52 of the expandable balloon 46 of the balloon catheter 42 is placed across the stenotic lesion in the body vessel, the expandable balloon 46 may then be inflated preferably with saline. For deployment of the expandable balloon 46 and the device 10, the outer catheter 60 is then retracted to expose the device 10 and angioplasty balloon at the stenotic lesion. The angioplasty balloon is inflated, and both the device 10 and balloon expands to break plaque of the stenotic lesion.

It is to be understood that the assembly described above is merely one example of an assembly that may be used to deploy the capturing device in a body vessel. Of course, other apparatus, assemblies, and systems may be used to deploy any embodiment of the capturing device without falling beyond the scope or spirit of the present invention.

Figure 5:
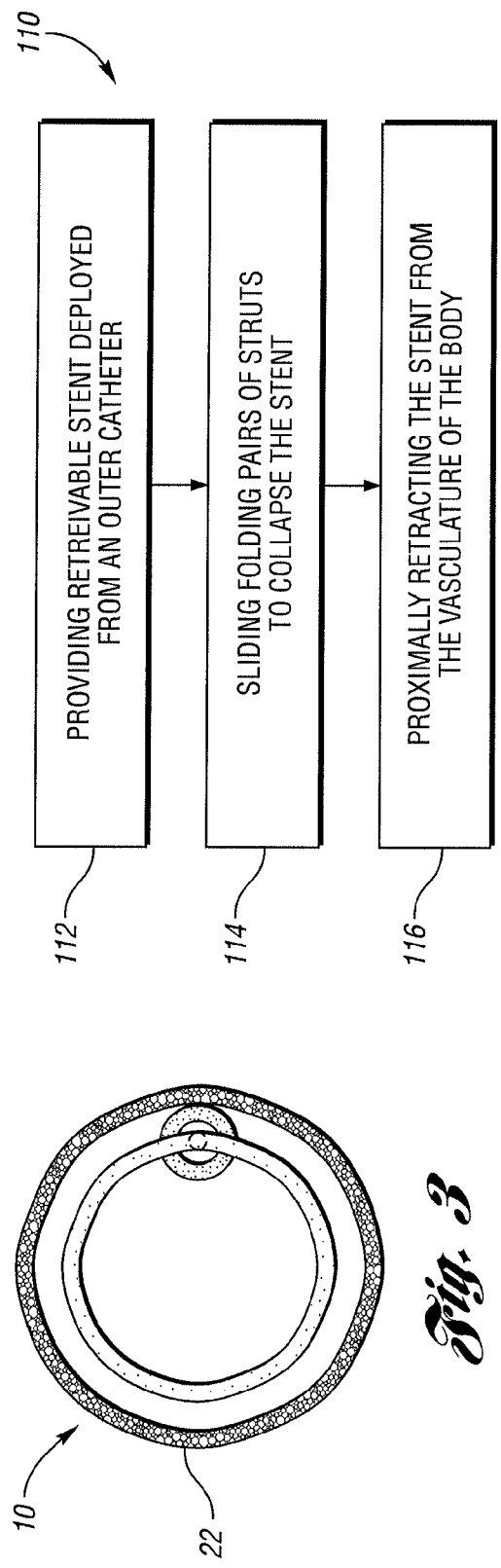
FIG. 5 is a flow chart depicting one method for treating a stenotic lesion in a body vessel.

FIG. 5 is a flow chart depicting one method 110 for treating a stenotic lesion in a body vessel. As shown, the method comprises providing in box 112 a retrievable stent deployed from an outer catheter at the stenotic lesion in the body vessel. One embodiment of the retrievable stent is the retrievable device 10 discussed above. The retrievable stent and a balloon catheter are preferably used to dilate a stenosis condition or stenotic lesion in a body vessel. Dilatation of a stenosed vessel may be accomplished in any desirable manner known in the art. After treatment of the stenotic lesion is completed, the balloon catheter is proximally retracted and removed from the vasculature. As discussed below, the stent may be also retrieved.

In this example, an outer catheter is used to fold the struts of the retrievable stent to its collapsed state for retrieval. The outer catheter is percutaneously inserted in the vasculature proximally adjacent the location of the stent. The outer catheter is then moved distally to receive the stent starting from the proximal portion thereof. In one example, the retrieval stem is pulled to proximally move the reticulation portion toward the distal end of the outer catheter, receiving the reticulation portion. Alternatively, the outer catheter may be distally moved toward the device to initiate folding of the struts. As the outer catheter longitudinally receives the stent, each pair of the struts is singly folded about each pivotal joint to move the reticulation portion in the collapsed state in box 114.

Once the stent is in its collapsed state, i.e., each pair of struts is folded about its respective pivotal joint, the stent may be retracted. As the outer catheter is proximally retracted to retract and retrieve the stent from the vasculature of the body vessel in box 116.

Figure 6:
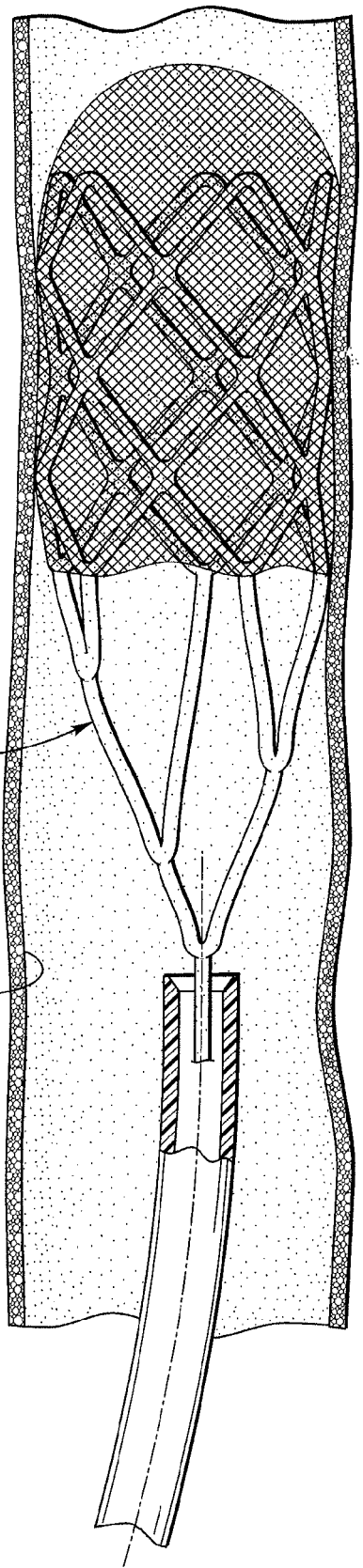
FIG. 6 is an environmental view of a retrievable device for treatment of a stenotic lesion in a body vessel in accordance with another embodiment of the present invention.

FIG. 6 illustrates a retrievable device 210 for capturing emboli during treatment of a stenotic lesion in a body vessel 211 in accordance with another embodiment of the present invention. As shown, the retrievable device 210 in this embodiment comprises components similar to the components mentioned in the retrievable device 10 of the embodiment mentioned above. For example, the device 210 includes a reticulation portion 212 having a plurality of struts 214 in a singly staggered configuration 216, an expandable body 230, and a retrieval stem 224 similar to the reticulation portion 12 having the plurality of struts 14, the expandable body 30, and the retrieval stem 24 of the retrievable device 10 mentioned above. As described in greater detail below, the retrievable device 210 of this embodiment is preferably used as an embolic protection device for capturing emboli during a stenotic procedure, e.g., angioplasty.

The retrieval device 210 of this embodiment further includes a filter portion 213 for capturing emboli during treatment of a stentic lesion, e.g., angioplasty. FIGS. 7a and 7b illustrate that the filter portion 213 has a lip 283. As shown, the lip 283 is attached to the distal portion 218 of the reticulation portion 212 and is disposed about the expandable body 230, defining an opening 284 of the filter portion when the device is in the expanded state for capturing emboli. The lip 283 may be attached to the distal portion 218 by any suitable means including sonic bonding, thermal bonding, or adhesive bonding. The filter portion 213 extends from the lip 283 to a filter end 286 formed to be a proximally facing concave shape. The opening 284 of the filter portion is configured to face toward the stenotic lesion.

As shown in FIG. 6, the expandable body of the device engages the vessel wall, placing the filter portion therebetween. This ensures that the filter portion captures emboli that disengage from the vessel wall during an angioplasty treatment upstream therefrom. In use, the device expands from the collapsed state to the expanded state, engaging the reticulation portion and expandable body with the body vessel. In turn, the lip of the filter portion expands to engage the vessel wall for capturing emboli during treatment of the stenotic lesion. After the need for such device in the vasculature passes, e.g., after angioplasty, the device may be retrieved by folding the struts of the reticulation portion and collapsing the device as described above.

The filter portion may be comprised of any suitable material to be used for capturing emboli from the stenotic lesion during treatment thereof. In one embodiment, the filter portion is made of connective tissue material for capturing emboli. In this embodiment, the connective tissue comprises extracellular matrix (ECM). As known, ECM is a complex structural entity surrounding and supporting cells that are found within mammalian tissues. More specifically, ECM comprises structural proteins (e.g., collagen and elastin), specialized protein (e.g., fibrillin, fibronectin, and laminin), and proteoglycans, a protein core to which are attached are long chains of repeating disaccharide units termed of glycosaminoglycans.

Most preferably, the extracellular matrix is comprised of small intestinal submucosa (SIS). As known, SIS is a resorbable, acellular, naturally occurring tissue matrix composed of ECM proteins and various growth factors. SIS is derived from the porcine jejunum and functions as a remodeling bioscaffold for tissue repair. SIS has characteristics of an ideal tissue engineered biomaterial and can act as a bioscaffold for remodeling of many body tissues including skin, body wall, musculoskeletal structure, urinary bladder, and also supports new blood vessel growth. In many aspects, SIS is used to induce site-specific remodeling of both organs and tissues depending on the site of implantation. In theory, host cells are stimulated to proliferate and differentiate into site-specific connective tissue structures, which have been shown to completely replace the SIS material in time.

In this embodiment, SIS is used to temporarily adhere the filter portion to the walls of a body vessel in which the device is deployed. SIS has a natural adherence or wettability to body fluids and connective cells comprising the connective tissue of a body vessel wall. Due to the temporary nature of the duration in which the device is deployed in the body vessel, host cells of the wall will adhere to the filter portion but not differentiate, allowing for retrieval of the device from the body vessel.

In other embodiments, the filter portion may also be made of a mesh/net cloth, nylon, polymeric material, Teflon™, or woven mixtures thereof without falling beyond the scope or spirit of the present invention.

While the present invention has been described in terms of preferred embodiments, it will be understood, of course, that the invention is not limited thereto since modifications may be made to those skilled in the art, particularly in light of the foregoing teachings.

The invention claimed is:

1. An assembly for treating a stenotic lesion in a body vessel, the assembly comprising:
   an outer catheter including a tubular body having a distal end; and
   a retrievable device coaxially disposable within the tubular body of the outer catheter and deployable through the distal end thereof for treatment of the stenotic lesion in the body vessel, the device comprising:
   a reticulation portion having a deployed state and a collapsed state, the reticulation portion forming an axial section of the retrievable device and including a plurality of struts and at least three longitudinally spaced single pivoting joints defining longitudinal reticulation sections therebetween, each pivoting joint of the reticulation portion being longitudinally offset from all other pivoting joints of the reticulation portion, each of the pivoting joints connecting a longitudinally coextending pair of the plurality of struts, the number of struts within each of the reticulation sections singly increasing from the reticulation section to a distally adjacent reticulation section along the entire reticulation portion, the pairs of struts of the reticulation portion being configured to fold along the longitudinal axis defining a collapsed state of the device for retrieval;
   an expandable body distally extending from the reticulation portion along an outer diameter for treatment of the stenotic lesion, the expandable body being configured to expand in the deployed state and collapsed in the collapsed state of the reticulation portion for retrieval; and a retrieval stem extending proximally from the reticulation portion for retrieval of the device in the collapsed state.

2. The assembly of claim 1 further comprising:

a balloon catheter comprising a tube member having an inner lumen, the balloon catheter further having an expandable balloon attached to and in fluid communication with the tube member for angioplasty at the stenotic lesion, the expandable balloon having distal and proximal portions;

a wire guide configured to be disposed through the inner lumen of the balloon catheter for percutaneous guidance through the body vessel; and an introducer sheath through which the outer catheter is inserted for percutaneous insertion to the body vessel.

3. The assembly of claim 2 wherein the balloon catheter further includes a proximal end, the proximal end having a hub in fluid communication with the balloon for fluid to be passed therethrough for inflation and deflation of the balloon during treatment of the stenotic lesion.

4. The assembly of claim 1 wherein the reticulation portion extends along the outer diameter.

5. The assembly of claim 1 wherein the number of struts on the reticulation portion increases in a singly staggered configuration along the longitudinal axis.

6. The assembly of claim 5 wherein the number of struts adjacent the retrieval stem of the device is one strut and the number of struts at the distal end is up to 10 struts.

7. The assembly of claim 1 wherein the outer diameter of the reticulation portion is substantially constant distally extending therealong to the expandable body.

8. The assembly of claim 1 wherein the retrieval stem extends proximally along the outer diameter of the reticulation portion.

* * * * *